(12) United States Patent
Khachik

(10) Patent No.: US 6,818,798 B1
(45) Date of Patent: Nov. 16, 2004

(54) PROCESS FOR MAKING A (3R,3'R)-ZEAXANTHIN PRECURSOR

(75) Inventor: Frederick Khachik, Rockville, MD (US)

(73) Assignee: University of Maryland, College Park, College Park, MD (US)

( * ) Notice: Subject to any disclaimer, the term of this patent is extended or adjusted under 35 U.S.C. 154(b) by 58 days.

(21) Appl. No.: 10/240,172

(22) PCT Filed: Jul. 11, 2000

(86) PCT No.: PCT/US00/18810

§ 371 (c)(1),
(2), (4) Date: Sep. 30, 2002

(87) PCT Pub. No.: WO01/83414

PCT Pub. Date: Nov. 8, 2001

Related U.S. Application Data

(60) Provisional application No. 60/201,703, filed on May 3, 2000.

(51) Int. Cl.⁷ .............................................. C07C 35/21
(52) U.S. Cl. ........................................ 568/816; 435/67
(58) Field of Search ............................ 568/816; 435/67

(56) References Cited

U.S. PATENT DOCUMENTS

| | | |
|---|---|---|
| 5,360,730 A | 11/1994 | Orndorff et al. |
| 5,382,714 A | 1/1995 | Khachik |
| 5,437,997 A | 8/1995 | Liao et al. |
| 5,523,494 A | 6/1996 | Torres-Cardona et al. |
| 5,780,693 A | 7/1998 | Bernhard et al. |
| 5,998,678 A | 12/1999 | Virgili et al. |
| 6,420,614 B1 * | 7/2002 | Eugster et al. ............ 568/816 |

FOREIGN PATENT DOCUMENTS

| | | |
|---|---|---|
| WO | WO 99/03830 A1 | 1/1999 |
| WO | WO 99/20587 A1 | 4/1999 |
| WO | WO 02/10128 A2 | 2/2002 |

OTHER PUBLICATIONS

Weedon, Pure Appl. Chem., vol. 47, pp 161–171 (1976).*

Barrett, A.G.M., et al., "Nucleophilic Substitution Reactions of (Alkoxymethylene)dimethylammonium Chloride," *J. Org. Chem. 63*:6273–6280, American Chemical Society (1998).

Bone, R.A., et al., "Stereochemistry of the Human Macular Carotenoids," *Invest. Ophthalmol. Vis. Sci. 34*:2033–2040, Association for Research in Vision and Ophthalmology (1993).

Khachik, F., et al., "Isolation and structural elucidation of the geometrical isomers of lutein and zeaxanthin in extracts from human plasma," *J. Chromatogr. Biomed. Appl. 582*:153–166, Elsevier Science B.V. (1992).

Khachik, F., et al., "Isolation, structural elucidation, and partial synthesis of lutein dehydration products in extracts from human plasma," *J. Chromatogr. B. Biomed. Appl. 670*:219–233, Elsevier Science B.V. (1995).

Mitsunobu, O., "The Use of Diethyl Azodicarboxylate and Triphenylphosphine in Synthesis and Transformation of Natural Products," *Synthesis, No. 1*:1–28, Georg Thieme Verlag (1981).

Seddon, J.M., et al., "Dietary Carotenoids, Vitamins A, C, and E, and Advanced Age–Related Macular Degeneration," *J. Am. Med. Assoc. 272*:1413–1420, American Medical Association (1994).

Sliwka, H.–R., and Liaaen–Jensen, S., "Partial Syntheses of Diastereomeric Carotenols," *Acta Chem. Scand. B 41*:518–525, The Chemmical Societies in Denmark, Finland, Norway and Sweden (1987).

Weedon, B.C.L., "Synthesis of Carotenoids and Related Polyenes," *Pure Appl. Chem. 47*:161–171, Pergamon Press (1976).

Widmer, E., et al., "87. Technical Procedures for the Syntheses of Carotenoids and Related Compounds from 6–Oxo–isophorone: Syntheses of (3R,3'R)–Zeaxanthin," *Helv. Chem. Acta 73*:861–867, Schweizerische Chemische Gesellschaft, Verlag Helvetica Chimica Acta (1990).

International Search Report for International Application No. PCT/US00/18810. 2 pages. ISA/US. Commissioner of Patents and Trademarks, Washington, DC (mailed Nov. 17, 2000).

* cited by examiner

*Primary Examiner*—Michael L. Shippen
(74) *Attorney, Agent, or Firm*—Sterne, Kessler, Goldstein & Fox, P.L.L.C.

(57) ABSTRACT

A process for the conversion of (3R,3'R,6'R)-lutein to 3'-epilutein, a carotenoid precursor for industrial production of naturally occurring (3R,3'R)-zeaxanthin, is disclosed.

70 Claims, No Drawings

PROCESS FOR MAKING A (3R,3'R)-ZEAXANTHIN PRECURSOR

BACKGROUND OF THE INVENTION

1. Field of the Invention

The invention is in the field of organic chemistry. The invention relates in part to a process for conversion of (3R,3'R,6'R)-lutein to (3R,3'S,6'R)-lutein (3'-Epilutein), a carotenoid precursor for industrial production of naturally occurring (3R,3'R)-zeaxanthin.

2. Related Art

As a result of a high intake of fruits and vegetables, 34 carotenoids and their metabolites are found in human serum and tissues at varying concentrations. Among these, only two dietary carotenoids, (3R,3'R,6'R)-lutein and (3R,3'R)-zeaxanthin, accumulate in the human retina. Epidemiological and experimental data suggest that the function of these carotenoids is to protect the photo-sensing cells in the human retina, and particularly macula, from exposure to short-wavelength blue light, and thus prevent age-related macular degeneration (AMD) (Bone, R. A., et al., *Invest. Ophthalmol. Vis. Sci.* 34:2033–2040 (1993); Seddon, J. M., et al., *J. Am. Med. Assoc.* 272:1413–1420 (1994)).

zeaxanthin is not commercially available. Currently the most promising route to this carotenoid is by chemical synthesis (Widmer et al., *Helv. Chim. Acta* 73:861–867 (1990)). However, the production of (3R,3'R)-zeaxanthin by total synthesis can be quite costly. Furthermore, the absence of possible residual contaminants in (3R,3'R) zeaxanthin prepared by synthesis must be established before this carotenoid can be safely used as a nutritional supplement or food coloring additive.

U.S. Pat. No. 5,523,494, European Patent Appl. 834536 and WO99/03830 describe the conversion of commercially available (3R,3'R,6'R) lutein or crude marigold meal to (3R,3S,meso)-zeaxanthin by base-catalyzed isomerization. (3R,3S,meso)-Zeaxanthin is absent from foods and its stereochemistry is different from that of dietary (3R,3'R)-zeaxanthin.

WO97/31894 describes a process wherein (3R,3'R,6'R)-lutein is first converted to (3R,3S,meso)-zeaxanthin and then is oxidized to β,β-carotene-3,3'-dione. In the final step of this process β,β-carotene-3,3'-dione is reduced with sodium or potassium borohydride to give a racemic mixture of (3R,3'R)-zeaxanthin, (3R,3'S,meso)-zeaxanthin, and (3S,3'S)-zeaxanthin (Scheme 1).

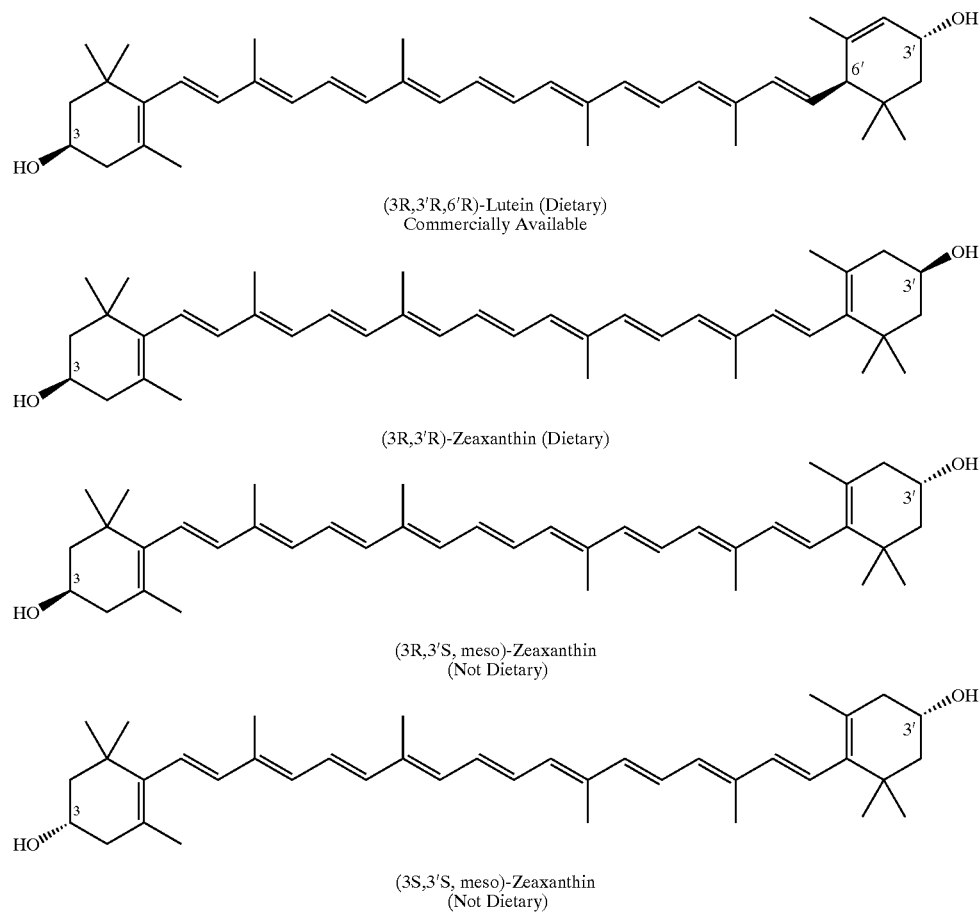

Scheme 1. Commercially available lutein and various configurational isomers of zeaxanthin.

(3R,3'R,6'R)-Lutein (Dietary)
Commercially Available (3R,3'R)-Zeaxanthin (Dietary)

(3R,3'S, meso)-Zeaxanthin
(Not Dietary)

(3S,3'S, meso)-Zeaxanthin
(Not Dietary)

While several patented processes for the industrial production of (3R,3'R,6'R)-lutein have been reported, (3R,3'R)-

Therefore with the exception of total synthesis, the other reported procedures either prepare (3R,3'S,meso)- zeaxanthin, which is not the natural dietary form of this carotenoid, or use chemical reagents and additional steps to prepare a racemic mixture of (3R,3'R)-zeaxanthin, (3R,3'S, meso)-zeaxanthin, and (3S,3'S)-zeaxanthin.

The present invention seeks to produce a precursor to (3R,3'R)-zeaxanthin in high diastereomeric excess (de). The precursor may then be transformed to (3R,3'R)-zeaxanthin by methods that are well known in the an.

SUMMARY OF THE INVENTION

According to the present invention, (3R,3'R,6'R)-lutein can be epimerized at C-3' in one convenient step using dilute acids to give a 1:1 diastereomeric mixture of 3'-epilutein and (3R,3'R,6'R)-lutein as shown in Scheme 2.

lutein and increase the de of 3'-epilutein in the mother liquor of this crystallization. Under these conditions, most of the (3R,3'R,6'R)-lutein is crystallized and can be recovered. At any stage of these processes, the recovered solid which is predominantly enriched in (3R,3'R,6'R)-lutein, can be recycled into the epimerization reaction.

The isolated 3'-epilutein may then be directly converted to naturally occurring (3R,3'R)-zeaxanthin by base-catalyzed isomerization (vide supra). All of the above separation procedures can be readily implemented on industrial scale with the advantage that the recovered (3R,3'R,6'R)-lutein can be recycled and epimerized to 3'-epilutein. The present invention does not employ any reagents other than commonly used organic solvents and acids which can be safety handled under mild conditions.

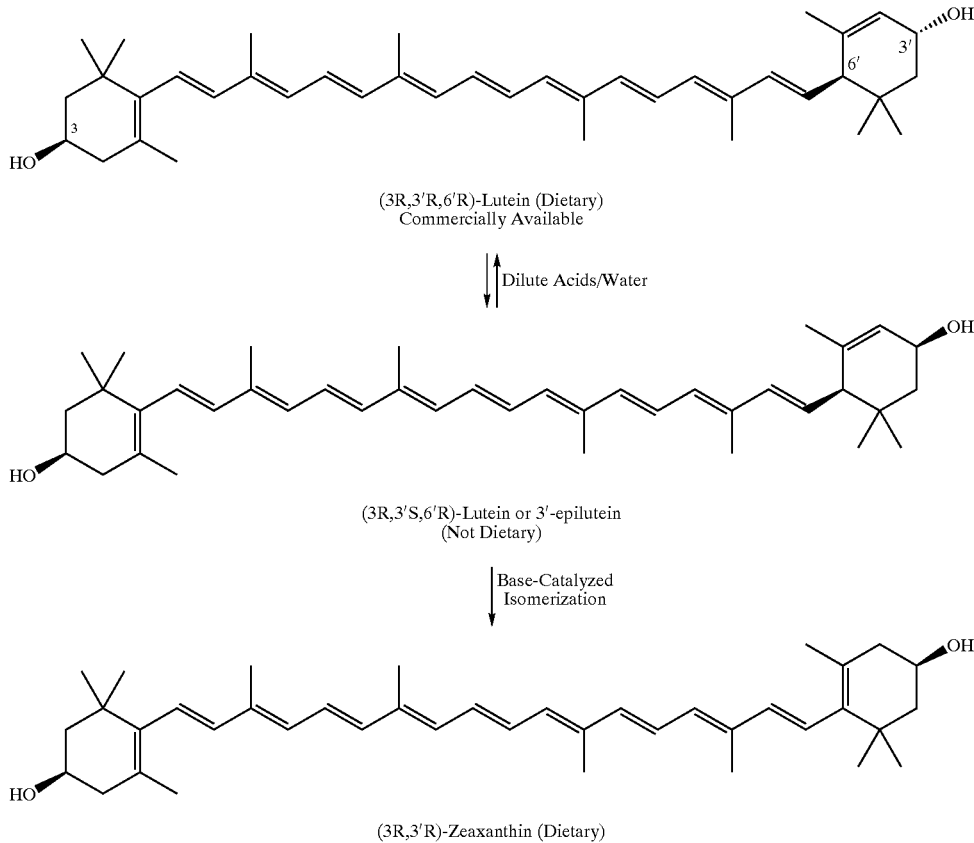

Scheme 2. Conversion of (3R,3¢P,6¢P)-lutein to (3R,3¢P)-zeaxanthin.

(3R,3'R,6'R)-Lutein (Dietary)
Commercially Available

Dilute Acids/Water (3R,3'S,6'R)-Lutein or 3'-epilutein
(Not Dietary)

Base-Catalyzed
Isomerization (3R,3'R)-Zeaxanthin (Dietary)

In the course of the work-up of the epimerization reaction, most of the (3R,3'R,6'R)-lutein is removed from this 1:1 mixture by filtration to produce a diastereomeric mixture in which the ratio of 3'-epilutein to (3R,3'R,6'R)-lutein is in the range of 3.4 to 3.5. A de of 54–90% can be accomplished by a) solvent extraction, b) preferential crystallization, c) Soxhlet extraction, d) enzymatic acylation, and e) supercritical extraction with carbon dioxide of either an about 1:1 mixture of (3R,3'R,6'R)-lutein and 3'-epilutein or the partially separated mixture (with ratio of 3.4 to 3.5).

Only enzymatic acylation of the 1:1 diastereomeric mixture of 3'-epilutein and (3R,3'R,6'R)-lutein, affords 3'-epilutein in 90% de whereas the other methods require additional purification to increase de of this carotenoid. The partially separated mixture can be subjected to low temperature crystallization to crystallize most of the (3R,3'R,6'R)-

In particular the invention relates to a method of epimerizing (3R,3'R,6'R)-lutein to give a mixture of (3R,3'R,6'R)-lutein and 3'-epilutein, comprising reacting (3R,3'R,6'R)-lutein in the presence of aqueous acid in a water miscible organic solvent to give a mixture of (3R,3'R,6'R)-lutein and 3'-epilutein.

The invention further relates to a method of purifying 3'-epilutein from a mixture of (3R,3'R,6'R)-lutein and 3'-epilutein comprising extracting the mixture of (3R,3'R, 6'R)-lutein and 3'-epilutein with an organic solvent and recovering the 3'-epilutein from the organic solvent.

The invention further relates to a method of purifying 3'-epilutein from a mixture of (3R,3'R,6'R)-lutein and 3'-epilutein comprising low temperature crystallization of the mixture in a $C_{1-4}$ alcohol and recovering the 3'-epilutein from the alcohol.

The invention further relates to a method of purifying 3'-epilutein from a mixture of (3R,3'R,6'R)-lutein and 3'-epilutein comprising:

(a) reacting a mixture of (3R,3'R,6'R)-lutein and 3'-epilutein with an acyl donor in the presence of lipase PS from *Pseudomonas cepacia* or lipase AK from *Pseudomonas fluorescens* in an first organic solvent;

(b) adding a second organic solvent to dissolve the mixture and removing the enzyme by filtration to give a filtrate;

(c) concentrating the filtrate to give a residue;

(d) adding a $C_{5-7}$ hydrocarbon or ether to the residue to give a solution in which 3'-epilutein and 3'-epilutein-3'-acetate are preferentially solubilized;

(e) filtering the solution to give a filtrate;

(f) hydrolyzing the 3'-epilutein-3'-acetate contained in the filtrate to give 3'-epilutein; and (g) recovering the 3'-epilutein;

thereby obtaining purified 3'-epilutein.

The invention further relates to a method of purifying 3'-epilutein from a mixture of (3R,3'R,6'R)-lutein and 3'-epilutein comprising extracting the mixture with super-critical carbon dioxide and evaporating the carbon dioxide to give purified 3'-epilutein.

The invention further relates to a method for producing 3'-epilutein comprising:

(a) epimerizing (3R,3'R,6'R)-lutein to 3'-epilutein in the presence of an aqueous acid in a water miscible organic solvent thereby giving a mixture of (3R,3'R,6'R)-lutein and 3'-epilutein; and (b) separating 3'-epilutein from (3R,3'R,6'R)-lutein.

The invention further relates to a method for converting (3R,3'R,6'R)-lutein to a mixture of 3'-epilutein and (3R,3'R,6'R)-lutein comprising:

(a) reacting (3R,3'R,6'R)-lutein with an aqueous acid in a solvent at ambient temperature to obtain a crude product;

(b) neutralizing the crude product with aqueous base; and (c) removing the water by partitioning the crude product into a water immiscible organic solvent;

thus obtaining a crude diastereomeric crystalline mixture of 3'-epilutein and (3R,3'R,6'R)-lutein.

The invention further relates to a method for the separation of 3'-epilutein from a mixture of 3'-epilutein and (3R,3'R,6'R)-lutein by enzymatic acylation, comprising reacting 3'-epilutein with an acyl donor in the presence of a lipase in pentane, hexane or TBME at 36° C. to convert 95% of 3'-epilutein to 3'-epilutein-3'-acetate while (3R,3'R,6'R)-lutein remains unreacted; subjecting the resulting 3'-epilutein-3'-acetate to hydrolysis with alcoholic potassium or sodium hydroxide at ambient temperature; removing the base by extracting the product with water and an organic solvent; and evaporating the solvent to obtain diastereomeric luteins comprising 95% 3'-epilutein and 5% (3R,3'R,6'R)-lutein as red crystals.

The invention further relates to a method of preparing 3'-epilutein-3'-acetate comprising reacting a mixture of (3R,3'R,6'R)-lutein and 3'-epilutein with an acyl donor in the presence of lipase PS from *Pseudomonas cepacia* or lipase AK from *Pseudomonas fluorescens*.

The invention further relates to a method for partial separation of 3'-epilutein from a diastereomeric mixture of 3'-epilutein and (3R,3'R,6'R)-lutein obtained according to the present invention by extracting the crude crystalline mixture with pentane or petroleum ether (b.p.=35–60° C.) in a Soxhlet apparatus to obtain a pentane or petroleum ether soluble fraction comprising of a diastereomeric mixture of 3'-epilutein (80%) and (3R,3'R,6'R)-lutein (20%), evaporating the solvents to obtain a crystalline mixture enriched in 3'-epilutein.

The invention further relates to a method for separating 3'-epilutein from a diastereomeric mixture of 3'-epilutein and (3R,3'R,6'R)-lutein comprising extracting the diastereomeric mixture of luteins with carbon dioxide thereby extracting most of 3'-epilutein with carbon dioxide and leaving behind most of the (3R,3'R,6'R)-lutein thus yielding a product consisting of 86% 3'-epilutein and 14% (3R,3'R,6'R)-lutein.

The invention further relates to a method for separating 3'-epilutein from a diastereomeric mixture of 3'-epilutein and (3R,3'R,6'R)-lutein comprising low temperature crystallization with an alcohol at −70° C. to crystallize most of the (3R,3'R,6'R)-lutein and increasing the purity of 3'-epilutein in the mother liquor of this crystallization; and evaporation of the alcohol; thus obtaining red crystals containing 94% 3'-epilutein and 6% (3R,3'R,6'R)-lutein.

DETAILED DESCRIPTION OF THE INVENTION

Reagents and Starting Materials

The crude saponified extract of marigold flower containing (3R,3'R,6'R)-lutein and several minor carotenoids may be prepared according to the process described in WO99/20587. (3R,3'R,6'R)-Lutein (97% purity) and several minor carotenoids may also be purified from this extract according to this procedure. Commercially available 70% pure (3R,3'R,6'R)-lutein may be obtained from Kemin Industries (Des Moines, Iowa). The crude saponified extract from Marigold flowers as well as the 70% and 97% pure lutein may all be successfully employed as the starting materials in the current invention. Lipase AK from *Pseudomonas fluorescens* ("Amano" 20) and lipase PS from *Pseudomonas cepacia* ("Amano") may be obtained from Amano Enzyme U.S.A. Co., Ltd. (Lombard, Ill.). Vinyl acetate (Aldrich Chemical Co., Milwaukee, Wis.) and all other commercial grade solvents were used without further purification.

The carotenoid composition of the 70% and 97% pure lutein is shown in Table 1. Purification of 70% lutein by crystallization results in the removal of other nutritionally important carotenoids which are present as minor constituents in marigold flowers. Therefore, the advantage of using the 70% pure lutein as starting material in this invention is that these minor carotenoids can be carried over and preserved in the final product. Alternatively, these minor carotenoids may be removed from the final product, (3R,3'R)-zeaxanthin, by crystallization.

TABLE 1

Carotenoid composition of 70% and 97% pure (3R,3'R,6'R)-lutein isolated from marigold flowers.[a]

| | Composition | |
|---|---|---|
| Marigold Carotenoids | 70% pure | 97% pure |
| (all-E,3R,3'R,6'R)-lutein | 91.8 | 95.0 |
| 3'-epilutein | 0.2 | 0.0 |
| Total Z-luteins | 0.93 | 0.0 |
| (all-E,3R,3'R)-zeaxanthin | 6.2 | 5.0 |
| Anhydroluteins (lutein dehydration products) | 0.06 | 0.0 |
| β-carotene | 0.36 | 0.0 |

TABLE 1-continued

Carotenoid composition of 70% and 97% pure (3R,3'R,6'R)-lutein isolated from marigold flowers.[a]

| Marigold Carotenoids | Composition | |
|---|---|---|
| | 70% pure | 97% pure |
| α-cryptoxanthin + β-cryptoxanthin | 0.05 | 0.0 |
| 3-hydroxy-β,ε-caroten-3'-one | 0.1 | 0.0 |
| ε,ε-carotene-3,3'-diol | 0.3 | 0.0 |

[a]The terms all-E (trans) and Z (cis) refer to in-chain geometrical isomers of carotenoids.

Conversion of (3R,3'R,6'R)-Lutein to (3R,3'R)-Zeaxanthin via 3'-Epilutein

There are two critical steps in conversion of commercially available dietary (3R,3'R,6'R)-lutein to (3R,3'R)-zeaxanthin (dietary), these are: 1) inversion of stereochemistry of (3R, 3'R,6'R)-lutein at C-3', and 2) double bond isomerization of the ε-end group to β-end group. While double bond isomerization has been studied extensively and as a result several patents for this transformation have been published, an economically viable method for the complete inversion of configuration of (3R,3'R,6'R)-lutein at C-3' has not been reported previously. Therefore, it is believed that the existing technology, at best, can only convert lutein into a racemic mixture of (3RS,3'RS)-zeaxanthin.

There are two widely used chemical methods for the inversion of stereochemistry of secondary chiral alcohols. The first is known as the Mitsunobu reaction (Mitsunobu, *Synthesis:* 1–28 (1981)), which employs diethyl azodicarboxylate, triphenylphosphine and an appropriate carboxylic acid to form a quaternary phosphonium salt. This is then allowed to react with a secondary chiral alcohol to cause the inversion of configuration. The Mitsunobu reaction has been previously used to convert lutein to 3'-epilutein in a very low isolated yield (Sliwka and Liaaen-Jensen, *Acta Chimica Scandinavica* B41:518–525 (1987)).

A second method uses imidate esters as potential replacements for diethyl azodicarboxylate and triphenylphosphine in the Mitsunobu reaction (Barrett, et al., *J. Org. Chem.* 63:6273–6280 (1998)). While it has been possible to increase the yield of the Mitsunobu reaction to about 20% under carefully dried reaction conditions, the reaction of imidate esters with lutein only resulted in elimination and the formation of lutein dehydration products. Because of this low yield and the fact that diethyl azodicarboxylate is unstable and potentially explosive, the preparation of 3'-epilutein from (3R,3'R,6'R)-lutein by the Mitsunobu reaction is not suitable for industrial scale production.

The present invention provides a convenient method for converting commercially available (3R,3'R,6'R)-lutein to 3'-epilutein. This method comprises: 1) epimerization of (3R,3'R,6'R)-lutein to an about 1:1 mixture of (3R,3'R,6'R)-lutein and 3'-epilutein and 2) at least partial separation of (3R,3'R,6'R)-lutein from 3'-epilutein. Immediately following the methods described herein for the at least partial separation of (3R,3'R,6'R)-lutein from 3'-epilutein, the de of 3'-epilutein may be increased to 88–90% by low temperature crystallization. 3'-Epilutein may then be converted to (3R, 3'R)-zeaxanthin by well known methods.

Separation of 3'-epilutein from (3R,3'R,6'R)-lutein may be accomplished by several methods. These methods include: a) solvent extraction, b) preferential crystallization, c) Soxhlet extraction, d) enzymatic acylation, and e) supercritical extraction with carbon dioxide. It has been found that by employing an appropriate solvent, the partial separation of 3'-epilutein and (3R,3'R,6'R)-lutein can be accomplished as part of the work-up of the epimerization reaction by preferential crystallization of the (3R,3'R,6'R)-lutein.

In a preferred embodiment, an about 1:1 mixture of 3'-epilutein and (3R,3'R,6'R)-lutein is separated by enzymatic acylation to give a 90% de of 3'-epilutein, thus dispensing the need for a separate partial separation.

1) Epimerization of (3R,3'R,6'R)-Lutein to 3'-Epilutein

This reaction employs an aqueous acid to effect the epimerization of (3R,3'R,6'R)-lutein to an about 1:1 mixture of 3'-epilutein and unchanged (3R,3'R,6'R)-lutein at ambient temperature in almost quantitative yield. Preferred aqueous acids for performing this process include hydrochloric, sulfuric, phosphoric acid, trifluoroacetic acid (TFA) and the like. It has been previously shown that the treatment of (3R,3'R,6'R)-lutein and/or 3'-epilutein with acid in the absence of water results in the formation of three lutein dehydration products which have been identified and characterized (Khachik, et al., *J. Chromatogr. Biomed. Application* 670:219–233 (1995)). However, in dilute aqueous acids the epimerization is nearly quantitative and only about 1% of the dehydration products of lutein are formed. Similarly, only about 1% in-chain isomerization of all-E (trans)-lutein to its Z(cis)-isomers is observed.

In a typical reaction, (3R,3'R,6'R)-lutein is treated with a mixture of dilute aqueous acid and a water miscible organic solvent overnight at ambient temperature. The reaction should be a single phase reaction. The ratio of dilute aqueous acid to water miscible organic solvent that is used in such an experiment may vary. Typically, enough water miscible organic solvent is added to dissolve (3R,3'R,6'R)-lutein. The aqueous acid is then added in an amount that allows (3R, 3'R,6'R)-lutein to remain in solution. The acid concentration used may be from about 0.2 N to about 1 N, most preferably about 0.3 N to 0.75 N. Preferred water miscible organic solvents for this reaction include tetrahydrofuran (THF), acetone and dimethylsulfoxide (DMSO). The acid is then neutralized and the product is partitioned into a second organic solvent. The organic solvents for this partition may be a lower dialkyl ether, a lower alkyl ester of acetic acid, methylene chloride, chloroform, 1,2-dichloroethane and carbon tetrachloride. Preferred ethers include diisopropyl ether, tert-butyl methyl ether (TBME), diethyl ether and the like. Preferred lower alkyl esters of acetic acid include ethyl acetate, methyl acetate, butyl acetate and the like.

The starting material for the epimerization reaction can be crude saponified extracts of marigold flowers, 70% commercially available lutein or 97% pure lutein. After the removal of the aqueous layer and partial evaporation of ethers, substantial quantities of (3R,3'R,6'R)-lutein preferentially precipitate or crystallize and can be removed by filtration. The resulting filtrate from this simple work-up is enriched in 3'-epilutein. For example, the composition of carotenoids in the filtrate from work-up with TBME is: (3R,3'R,6'R)-lutein (21%), 3'-epilutein (73%), (3R,3'R)-zeaxanthin (1%), and other minor carotenoids (5%). The composition of carotenoids in the solids from this work-up is: (3R,3'R,6'R)-lutein (64%), 3'-epilutein (19%), (3R,3'R)-zeaxanthin (10%), and other minor carotenoids (7%); these recovered carotenoids can be recycled into the epimerization step. If no attempt is made to partially separate (3R,3'R, 6'R)-lutein from 3'-epilutein during work-up, the composition of the crude products from epimerization of 70% and 97% pure (3R,3'R,6'R)-lutein is as follows (Table 2):

TABLE 2

Carotenoid composition of the crude products from epimerization of 70% and 97% pure (3R,3'R,6'R)-lutein with aqueous hydrochloric acid.[a]

| Carotenoids | Composition after epimerization | |
|---|---|---|
| | 70% pure | 97% pure |
| (all-E,3R,3'R,6'R)-lutein | 44.0 | 46.5 |
| 3'-epilutein | 44.0 | 46.5 |
| total Z-luteins[b] | 2.7 | 1.0 |
| (all-E,3R,3'R)-zeaxanthin | 6.0 | 5.0 |
| Anhydroluteins (lutein dehydration products) | 1.3 | 1.0 |
| β-carotene | 1.5 | Not Detected |
| α-cryptoxanthin + β-cryptoxanthin | 0.05 | Not Detected |
| 3-hydroxy-β,ε-caroten-3'-one | 0.05 | Not Detected |
| ε,ε-carotene-3,3'-diol | 0.4 | Not Detected |

[a]The terms all-E (trans) and Z (cis) refer to in-chain geometrical isomers of carotenoids.
[b]The Z-isomers were: 9Z-lutein, 9'Z-lutein, 13Z-lutein, 13'Z-lutein, 13Z, 13'Z-lutein.

2) Separation of (3R,3'R,6'R)-Lutein from 3'-Epilutein

3'-Epilutein may be separated or purified from a mixture of 3-epilutein and (3R,3'R,6'R)-lutein by any one of a number of methods described herein and combinations thereof. It is intended that the terms "separating" and "purifying" mean that at least a partial separation or purification is achieved.

Separation and removal of (3R,3'R,6'R)-lutein from 3'-epilutein according to the present invention can give a purity of up to 95% (90% de) of 3'-epilutein. The starting material can be either an about 1:1 mixture of (3R,3'R,6'R)-lutein and 3'-epilutein or the partially separated mixture of the two as described above. According to the present invention, at least a partial separation is achieved. Preferably, the 3'-epilutein has a de greater than 50%.

In the course of handling and work-up of the crude products from epimerization of (3R,3'R,6'R)-lutein, it was discovered that 3'-epilutein is slightly more soluble than (3R,3'R,6'R)-lutein in non-polar hydrocarbon solvents. Such solvents include pentane, hexane, heptane, cyclohexane, petroleum ether (b.p.=35–60° C.) and the like. Based on this difference in solubility behavior, a number of processes were developed which allowed the partial separation of 3'-epilutein from (3R,3'R,6'R)-lutein. These methods are a) solvent extraction, b) preferential crystallization, c) Soxhlet extraction, d) enzymatic acylation, and e) supercritical extraction with carbon dioxide. When each of these methods is applied separately to a 1:1 mixture of (3R,3'R,6'R)-lutein and 3'-epilutein, the partial separation of these carotenoids was accomplished and 3'-epilutein was obtained in 77–95% enrichment. Among these, enzymatic acylation was found to be the most effective and afforded 3'-epilutein in 90% de. The enrichment of 3'-epilutein in poorly separated mixtures may be further increased by low-temperature crystallization of (3R,3'R,6'R)-lutein from a $C_{1-4}$ alcohol. Alcohols suitable for this crystallization include ethanol, methanol, propanol, 2-propanol and the like. The temperature at which the crystallization may be performed is between about −80° C. and about −40° C. Preferably, the crystallization is performed at about −70° C.

With the exclusion of the minor carotenoids, the mother liquor from this crystallization, in some cases, was shown to consist of up to 94% of 3'-epilutein and 6% (3R,3'R,6'R)-lutein.

a) Solvent Extraction/Preferential Crystallization

As pointed out above, the solubility of 3'-epilutein in solvents such as pentane, hexane, heptane, and petroleum ether (b.p.=35–60° C.) is much higher than that of (3R,3'R, 6'R)-lutein. However, large scale separation with these non-polar hydrocarbons alone would require large volumes of solvents and is not practical. For example, the low solubility of 3'-epilutein in hexane (13 ml/mg) is indicative of the large volumes of this solvent needed for the partial separation of 3'-epilutein from (3R,3'R,6'R)-lutein by virtue of their differential solubilities. Therefore, a co-solvent may be employed to increase the solubility of 3'-epilutein and at the same time reduce the volume of the hydrocarbon solvent. Among a number of solvents examined, the combination of a $C_{4-6}$ ether and a $C_{5-7}$ non-polar hydrocarbon solvent was found to be most effective. Preferred ethers include diethyl ether, TBME, diisopropyl ether and the like. Preferred non-polar hydrocarbon solvents include pentane, hexane, heptane, petroleum ether and the like. The preferred petroleum ether is that fraction which boils at 35–60° C. The ratio of non-polar hydrocarbon solvent (or petroleum ether) to ether may range from 4:1, to about 2:1, more preferably, about 3:1. One of ordinary skill in the art may determine other ratios with no more than routine experimentation.

In a typical solvent extraction procedure, an about 1:1 mixture of 3'-epilutein and (3R,3'R,6'R)-lutein is stirred with a mixture of an ether and a non-polar hydrocarbon to dissolve most of the 3'-epilutein in the mixture while (3R, 3'R,6'R)-lutein, for the most part, remains as crystals and is removed by filtration. The mother liquor from this solvent extraction is enriched in 3'-epilutein. The ratio of 3'-epilutein to (3R,3'R,6'R)-lutein in the filtrate is in the range of 3.4 to 3.5. The mother liquor is then evaporated and subjected to low-temperature crystallization using an alcohol such as ethanol or methanol to further remove (3R,3'R,6'R)-lutein. With the exclusion of the minor carotenoids, the mother liquor from this crystallization consists of 3'-epilutein (94%) and (3R,3'R,6'R)-lutein (6%). Based on this observation, an about 1:1 mixture of (3R,3'R,6'R)-lutein and 3'-epilutein was stirred with an alcohol to evaluate the suitability of this single solvent for the partial separation of these carotenoids. It was revealed that either solvent can affect the partial separation of these carotenoids. The ratio of 3'-epilutein to (3R,3'R,6'R)-lutein in the alcohol soluble fraction was 3.9/1. The solids were mostly enriched in lutein ((3R,3'R,6'R)-lutein/3'-epilutein=5.2/1). The results of the partial separation of 3'-epilutein from (3R,3'R,6'R)-lutein by solvent extraction are shown in Table 3.

Preferred alcohols for the single solvent extraction include ethanol, methanol, propanol, 2-propanol and the like. In general, the above-mentioned extractions may be performed at a temperature between 15° C. and 35° C. Preferably, the extractions are performed at room temperature. The period of time required to perform the extraction may vary from about 15 minutes to several hours, most preferably 30 minutes to 1 hour. One of ordinary skill in the art may determine the amount of time necessary for complete extraction with no more than routine experimentation.

The amount of solvent needed to separate a mixture of (3R,3'R,6'R)-lutein from 3'-epilutein may be defined in terms of milliliters of non-polar hydrocarbon solvent and milliliters of the ether, per gram of (3R,3'R,6'R)-lutein/3'-epilutein mixture; or the milliliters of alcohol per gram of (3R,3'R,6'R)-lutein/3'-epilutein mixture. When a mixture of a non-polar hydrocarbon solvent and an ether is used to effect the separation of (3R,3'R,6'R)-lutein from 3'-epilutein, the amount of non-polar hydrocarbon solvent may be from about 80 to about 120 ml and the amount of ether may be from about 20 to about 60 ml. Preferably, the amount of non-polar hydrocarbon solvent is about 90 ml and the amount of ether is about 30 ml. When an alcohol is used as a single solvent to effect the partial separation of (3R,3'R, 6'R)-lutein from 3'-epilutein, the amount of solvent may be from about 60 to about 150 ml, more preferably about 90 to 110 ml.

TABLE 3

Carotenoid composition in solid and liquid fractions obtained from partial separation of an about 1:1 mixture of (3R,3'R,6'R)-lutein and 3'-epilutein by solvent extraction.

| Carotenoids (%) in the epimerized mixture of 70% pure (3R,3'R,6'R)-lutein | Carotenoid Composition (%) of the Solid and Liquid Fractions from Extraction of an Epimeric Mixture of (3R,3'R,6'R)-Lutein and 3'-Epilutein with Several Solvents | | | | | |
|---|---|---|---|---|---|---|
| | Hexane/ TBME:3/1 | | Pentane/Diethyl ether:2/1 | | Ethanol | |
| | Solid | Liquid | Solid | Liquid | Solid | Liquid |
| (3R,3'R,6'R)-lutein (44%) | 64 | 21 | 64 | 21 | 73 | 18 |
| 3'-Epilutein (44%) | 19 | 73 | 23 | 72 | 14 | 71 |
| (3R,3'R)-Zeaxanthin (6%) | 10 | 1 | 10 | 0.4 | 8 | 4 |
| Other minor Carotenoids (6%) | 7 | 5 | 3 | 6.6 | 5 | 7 |

Preferential crystallization is another technique that may be used to separate 3'-epilutein from (3R,3'R,6'R)-lutein. As was the case with the above-mentioned solvent extraction, preferential crystallization takes advantage of the differential solubilities of 3'-epilutein and (3R,3'R,6'R)-lutein. In this embodiment, a mixture of 3'-epilutein and (3R,3'R,6'R)-lutein may be completely dissolved in a solvent or mixture of solvents. Then, a second solvent may be added which will cause (3R,3'R,6'R)-lutein to preferentially crystallize or precipitate out of solution. The resulting solution, rich in 3'-epilutein, may be separated from the precipitate, rich in (3R,3'R,6'R)-lutein, by filtration. In a preferred embodiment, the preferential crystallization technique is carried out as part of the workup from the epimerization reaction.

b) Soxhlet Extraction

Soxhlet extraction of a 1:1 diastereomeric mixture of (3R,3'R,6'R)-lutein and 3'-epilutein with non-polar hydrocarbons allowed the partial separation of these carotenoids. Preferred $C_{5-7}$ non-polar hydrocarbons and petroleum ether for this extraction include petroleum ether (b.p.=35–60°), pentane, hexane, heptane and the like. The period of time required to perform the extraction may vary from about 3 to 8 hours, most preferably 4 to 6 hours. One of ordinary skill in the art may determine the amount of time necessary for complete extraction with no more than routine experimentation.

The amount of non-polar hydrocarbon solvent necessary to effect the partial separation of (3R,3'R,6'R)-lutein from 3'-epilutein is from 100 to about 500 ml per gram of mixture, more preferably about 200 to 400 ml per gram of mixture. The non-polar hydrocarbon solvent used may be a single solvent or a mixture of two or more of the above-mentioned solvents.

When Soxhlet extraction was carried out with hexane or heptane, the separation was quite poor and significant amounts of Z-isomers of diastereomeric luteins and (3R, 3'R)-zeaxanthin were found in the hydrocarbon soluble fractions. However, the best results were obtained by extraction of (3R,3'R,6'R)-lutein and 3'-epilutein with pentane (b.p.=36° C.) or petroleum ether. After 4 hours, more than 90% of the 3'-epilutein was extracted from the mixture by these solvents. These extracts were shown by HPLC to consist of 3'-epilutein (77%), (3R,3'R,6'R)-lutein (19%), total Z-luteins (2%), and anhydrolutein (2%). The remaining solid consisted of 3'-epilutein (20%), (3R,3'R,6'R)-lutein (70.5%), and zeaxanthin (9.5%). It appears that Z-luteins and anhydrolutein, which are present in the starting material, are completely removed by Soxhlet extraction in the non-polar hydrocarbon soluble fraction while (3R,3'R)-zeaxanthin is not extracted and remains in the solid phase.

c) Enzymatic Acylation (3R,3'R,6'R)-Lutein and 3'-epilutein can be best separated by enzymatic acylation in an organic solvent in the presence of a lipase and an acyl donor.

Preferred lipases for the acylation include AK from *Pseudomonas fluorescens* ("Amano" 20) and lipase PS from *Pseudomonas cepacia* ("Amano"). Preferred organic solvents for the acylation include pentane, hexane, TBME, petroleum ether and the like. Acyl donors include $C_{2-3}$ vinyl acetates. Preferred $C_{2-3}$ vinyl acetates include vinyl acetate, isopropenyl acetate and the like. The period of time required to completely acylate 3'-epilutein may vary from about 36 to 96 hours, most preferably about 48 to 72 hours. One of ordinary skill in the art may determine the amount of time necessary to complete the acylation reaction with no more than routine experimentation.

The weight of lipase needed to conduct the enzymatic acylation per gram of (3R,3'R,6'R)-lutein/3'-epilutein mixture may vary from about 0.1 to 0.6 g, preferably about 0.2 to 0.4 g. One of ordinary skill in the art may determine the weight of lipase necessary to conduct the enzymatic acylation per gram of (3R,3'R,6'R)-lutein/3'-epilutein mixture with no more than routine experimentation.

While (3R,3'R,6'R)-lutein and (3R,3'R)-zeaxanthin are not acylated with lipase AK or lipase PS, 3'-epilutein undergoes acylation at C-3' to give 3'-epilutein-3'-acetate. As mentioned above, due to the difference in solubility between (3R,3'R,6'R)-lutein and 3'-epilutein, the enzymatic acylation can be readily carried out in the above-mentioned organic solvents. The product of this enzymatic reaction, 3'-epilutein-3'-acetate, is highly soluble in the non-polar organic solvents and as a result can be effectively removed from (3R,3'R,6'R)-lutein by solvent extraction. This extraction is performed at a temperature between 0° C. and room temperature. Preferably, the extraction is performed at 0 to 10° C. Preferred organic solvents for the extraction include, but are not limited to, $C_{4-6}$ ethers, lower alkyl esters of acetic acid, and $C_{5-7}$ non-polar hydrocarbons or petroleum ether (b.p.=35–60'). Preferred ethers include diethyl ether, TBME, diisopropyl ether and the like. Preferred non-polar hydrocarbons include pentane, hexane, heptane and the like. Preferred esters include ethyl acetate, methyl acetate, butyl acetate and the like.

When the enzymatic acylation was attempted on the diastereomeric mixture of (3R,3'R,6'R)-lutein and 3'-epilutein prepared from 70% pure lutein, no reaction was observed. This is presumably due to the presence of impurities in 70% pure (3R,3'R,6'R)-lutein which may be carried over in the products of the epimerization reaction. Therefore, prior to enzymatic acylation, an about 1:1 mixture of (3R,3'R,6'R)-lutein and 3'-epilutein prepared from 70% pure lutein, is purified for example by flash column chromatography on a silica gel column using hexane and acetone as eluent and all the carotenoid fractions are combined and evaporated. Alternatively, if the diastereomeric mixture of (3R,3'R,6'R)-lutein and 3'-epilutein is prepared from the 97% pure (3R,3'R,6'R)-lutein (Table 2), and this is then employed as the starting material for the enzymatic acylation, the reaction proceeds smoothly and no additional purification is needed.

In a typical procedure, an epimeric mixture of (3R,3'R, 6'R)-lutein and 3'-epilutein prepared from 97% pure lutein is acylated with vinyl acetate in the presence of lipase AK or PS at about 36° C. in pentane or hexane. After 48 h with lipase AK, approximately 5% of 3'-epilutein remains unreacted. However, lipase PS react much more slowly than lipase AK and after 72 h, 10% of 3'-epilutein is found unesterified. At the end of these reactions, an organic solvent (e.g., THF, diethyl ether, TBME, diisopropyl ether) is added to solubilize all the carotenoids, the enzyme is removed by filtration, and the product is evaporated to dryness. The residue is washed with pentane or hexane at about 0° C. to remove 3'-epilutein-3'-acetate, leaving behind (3R,3'R,6'R)-lutein and (3R,3'R)-zeaxanthin. After hydrolysis of the 3'-epilutein-3'-acetate, for example with alcoholic alkali, the product consists of mainly 3'-epilutein and (3R,3'R,6'R)-lutein is only present as a minor diastereomer. Preferred alkali for the hydrolysis of 3'-epilutein-3'-acetate include potassium hydroxide, sodium hydroxide, calcium hydroxide, ammonium hydroxide, methanolic ammonia and the like.

The results of the enzymatic acylation with lipase AK and PS and the de of 3'-epilutein in the final product is summarized in Table 4.

ence between (3R,3'R,6'R)-lutein and 3'-epilutein, the use of a hydrocarbon (e.g., hexane, heptane) or an alcohol (e.g., ethanol, methanol) cosolvent facilitates the extraction of 3'-epilutein in large-scale operations.

The extraction with supercritical carbon dioxide is preferably performed at a pressure from about 300 to about 350 atmospheres.

3) Enrichment of 3'-Epilutein in the Partially Separated Mixture by Low Temperature Crystallization of (3R,3'R, 6'R)-Lutein As described above, the initial separation of an epimeric mixture of (3R,3'R,6'R)-lutein and 3'-epilutein by one of the methods described above results in partial separation of these carotenoids. With the exception of enzymatic acylation, which resulted in the best separation of diastereomeric luteins, separation of these carotenoids by the other methods results only in partially separated mixtures. Therefore, depending on the separation method, the enrichment of 3'-epilutein in these mixtures is in the range of 77–86% and the remainder is (3R,3'R,6'R)-lutein (14–23%). The de of 3'-epilutein in these mixtures can be increased by low temperature crystallization of (3R,3'R,6'R) lutein from a $C_{1-4}$ alcohol. Alcohols suitable for this crystallization include ethanol, methanol, propanol, 2-propanol and the like. The temperature at which the crystallization may be performed is between −80° C. and −40° C. Preferably, the

TABLE 4

Carotenoid composition of the products separated from enzymatic acylation of an epimeric mixture of (3R,3'R,6'R)-lutein and 3'-epilutein.

| Epimeric Mixture of (3R,3'R,6'R)-Lutein and 3'-Epilutein Employed as the Starting Material | Composition (%) of Carotenoids in the Crude Products Separated from Enzymatic Acylation of (3R,3'R,6'R)-Lutein and 3'-Epilutein | | | |
|---|---|---|---|---|
| | Lipase AK | | Lipase PS | |
| Carotenoid Composition (%) | Pentane Insoluble | Pentane Soluble After Hydrolysis | Hexane Insoluble | Hexane Soluble After Hydrolysis |
| 3'-Epilutein (46.5) | 4.7 | 91.0 (90% de)[a] | 9.0 | 82.0 (70% de)[a] |
| (3R,3'R,6'R)-Lutein (46.5) | 86.0 | 4.8 | 80.0 | 14.0 |
| (3R,3'R)-Zeaxanthin (5.0) | 9.3 | N.D.[b] | 11.0 | N.D.[b] |
| Total Z-Luteins (1.0) | N.D.[b] | 2.1 | N.D.[b] | 2.0 |
| Anhydrolutein (1.0) | N.D.[b] | 2.1 | N.D.[b] | 2.0 |

[a]Refers to de of 3'-epilutein in the mixture.
[b]Not detected.

Enzymatic acylation with lipase AK and lipase PS affords 3'-epilutein in 90% and 70% de, respectively. It is imperative to point out that while TBME could also be employed as solvent with these enzymes with nearly the same results, THF did not promote the acylation of 3'-epilutein.

d) Extraction with Supercritical Carbon Dioxide

The partial separation of (3R,3'R,6'R)-lutein and 3'-epilutein was also found to be quite feasible by the use of supercritical fluid extraction with carbon dioxide. When this experiment was conducted on a 5 mg scale, it was discovered that the solubility of 3'-epilutein in supercritical carbon dioxide was by far greater than that of (3R,3'R,6'R)-lutein and (3R,3'R)-zeaxanthin.

Extraction with supercritical carbon dioxide resulted in extraction of 85% of the 3'-epilutein. The composition of carotenoids in the extracted fraction was: 3'-epilutein (83%), (3R,3'R,6'R)-lutein (13%), Z-luteins (2%), and anhydrolutein (2%). Therefore, under these conditions, 3'-epilutein can be obtained in 73% de. Based on the solubility differcrystallization is performed at about −70° C. The crystallization is performed using the aforementioned preferred solvents in an amount from about 100 to 180 ml per gram of (3R,3'R,6'R)-lutein/3'-epilutein mixture, preferably from 130 to 150 ml per gram of (3R,3'R,6'R)-lutein/3'-epilutein mixture. In ethanol, for example, nearly half of the 3'-epilutein with 94% purity remains soluble at low temperature and is removed by filtration. The solids from this crystallization consists of a mixture of 3'-epilutein (80%) and (3R,3'R,6'R)-lutein (20%) which can be recycled and subjected to further purification by low temperature crystallization.

4) Isomerization of 3'-Epilutein to (3R,3'R)-Zeaxanthin

3'-Epilutein obtained by the methods described above may subsequently be converted to (3R,3R')-zeaxanthin by base catalyzed isomerization (see Scheme 2) by the methods described in U.S. Pat. No. 5,780,693 and European Patent Appl. 834536. Briefly, conversion of 3'-epilutein to (3R, 3R')-zeaxanthin by base-catalyzed isomerization involves heating 3'-epilutein in a mixture of aqueous alkali metal hydroxide solution in either dimethyl sulphoxide (DMSO) or a saturated aliphatic and/or aromatic hydrocarbon solvent, at temperatures above 50° C. If a hydrocarbon solvent is used, the process is carried out in the presence of a phase transfer catalyst. Preferred hydrocarbon solvents include pentane, hexane, heptane, high boiling petroleum ether, benzene, toluene or mixtures thereof. Preferred alkali metal hydroxides include sodium hydroxide and potassium hydroxide. Phase transfer catalysts that may be used include tricaprylmethylammonium chloride, tetra-(n-butyl)-ammonium hydrogen sulfate, benzalkonium chloride, benzyl tri-(n-butyl)ammonium bromide, tri-(n-butyl) ammonium iodide and the like.

Having now generally described this invention, the same will be understood by reference to the following examples which are provided herein for purposes of illustration only and are not intended to be limiting unless otherwise specified.

EXAMPLE 1

Epimerization of (3R,3'R,6'R)-Lutein to 3'-Epilutein with Aqueous Hydrochloric Acid In a typical process, 7 g of commercially available (3R,3'R,3'R)-lutein (70% pure) in 600 ml of tetrahydrofuran (THF) is stirred with 250 ml of an aqueous solution of hydrochloric acid (0.3 N, pH=0.56 at 23° C.) at ambient temperature under nitrogen. The course of the reaction is followed by High Performance Liquid Chromatography (HPLC) according to a published procedure (Khachik, et al., J. Chromatogr. Biomed. Application 582:153–166 (1992)). According to HPLC after 24 h, the crude product consists of a 1:1 diastereomeric mixture of (3R,3'R,6'R)-lutein and 3'-epilutein. An aqueous solution of 5% sodium bicarbonate (100 ml) is added and the crude product is partitioned into 300 ml of TBME containing 1% (v/v) triethylamine. Instead of TBME other organic solvents such as diethyl ether or ethyl acetate can also be used with the same results. The aqueous layer is removed and the organic layer is washed with water (100 ml) and dried over sodium sulfate. The solvent is removed in vacuo below 40° C. and the residue (6.7 g) is used without purification in the next step. Similarly, the 97% pure lutein was epimerized at C-3' to a 1:1 diastereomeric mixture with identical results.

An analytical sample of 3'-epilutein was separated from (3R,3'R,6'R)-lutein by preparative HPLC from the crude product of epimerization and its identity was confirmed by Ultraviolet-Visible (UV-Vis) spectrophotometry, mass spectrometry (MS), and nuclear magnetic resonance (NMR) spectroscopy according to a published procedure (Khachik, et al. J. Chromatogr. Biomed. Application 582:153–166 (1992)).

EXAMPLE 2

Epimerization of (3R,3'R,6'R)-Lutein to 3'-Epilutein with Aqueous Sulfuric Acid

The epimerization reaction of (3R,3'R,6'R)-lutein with aqueous sulfuric acid and phosphoric acids also produced identical results. Only the example using sulfuric acid is described here.

(3R,3'R,3'R)-Lutein (3.0 g of 70% pure) in THF (250 ml) is stirred with 100 ml of an aqueous solution of sulfuric acid (0.75 N, pH=0.44 at 23° C.) at ambient temperature under nitrogen. According to HPLC the reaction is completed after 28 h. An aqueous solution of 5% sodium bicarbonate (50 ml) is added and the crude product is partitioned into 150 ml of TBME containing 1% (v/v) triethylamine. The aqueous layer is removed and the organic layer is washed with water (50 ml), dried over sodium sulfate, and evaporated to dryness under reduced pressure to give 2.80 g of an about 1:1 mixture of (3R,3'R,6'R)-lutein and 3'-epilutein.

EXAMPLE 3

Separation of 3'-Epilutein from (3R,3'R,6'R)-Lutein by Solvent Extraction with TBME 0.100 g of an about 1:1 mixture of 3'-epilutein and (3R,3'R,6'R)-lutein (prepared from 70% pure (3R,3'R,6'R)-lutein, Table 2) was suspended in TBME (3 ml) and hexane (9 ml) in a centrifuge tube. The mixture was stirred at room temperature for 30 minutes and the tube was centrifuged. The solid was removed and evaporated under high vacuum to give dark orange crystals (54 mg) of a mixture of (3R,3'R,6'R)-lutein (64%), 3'-epilutein (19%), (3R,3'R)-zeaxanthin (10%), and other minor carotenoids (7%); the composition of these carotenoids in the mixture was determined by HPLC. The filtrate was evaporated to give 46 mg of a dark red residue which was shown by HPLC to consist of a mixture of 3'-epilutein (73%), (3R,3'R,6'R) lutein (21%), (3R,3'R)-zeaxanthin (1%), and other minor carotenoids (5%).

EXAMPLE 4

Separation of 3'-Epilutein from (3R,3'R,6'R)-Lutein by Solvent Extraction with Diethyl Ether 0.106 g of an about 1:1 mixture of 3'-epilutein and (3R,3'R,6'R)-lutein (prepared from 70% pure (3R,3'R,6'R)-lutein, Table 2) was suspended in diethyl ether (5 ml) and pentane (10 ml) in a centrifuge tube. The mixture was stirred at room temperature for 30 minutes and the tube was centrifuged. The solid (56 mg) was shown by HPLC to consist of (3R,3'R,6'R)-lutein (64%), 3'-epilutein (23%), (3R,3'R)-zeaxanthin (10%), and several other minor carotenoids (3%). The filtrate was evaporated to give 50 mg of a dark red solid which according to HPLC consisted of a mixture of 3'-epilutein (72%), (3R,3'R,6'R)-lutein (21%), (3R,3'R)-zeaxanthin (0.4%), and other minor carotenoids (6.6%).

EXAMPLE 5

Separation of 3'-Epilutein from (3R,3'R,6'R)-Lutein by Solvent Extraction with Ethanol 0.20 g of an about 1:1 mixture of 3'-epilutein and (3R,3'R,6'R)-lutein (prepared from 70% pure (3R,3'R,6'R)-lutein, Table 2) was treated with ethanol (20 ml) in a centrifuge tube. The mixture was stirred at room temperature for 30 minutes and the tube was centrifuged. The solid (94 mg) was shown by HPLC to consist of (3R,3'R,6'R)-lutein (73%), 3'-epilutein (14%), and (3R,3'R)-zeaxanthin (8%). The filtrate was evaporated to dryness to give 106 mg of a dark solid which according to HPLC consisted of a mixture of 3'-epilutein (71%), (3R,3'R,6'R)-lutein (18%), (3R,3'R)-zeaxanthin (4%), and other minor carotenoids (7%).

EXAMPLE 6

Separation of 3'-Epilutein from (3R,3'R,6'R)-Lutein by Soxhlet Extraction 0.10 g of an about 1:1 mixture of (3R,3'R,6'R)-lutein and 3'-epilutein obtained from epimerization of a 97% pure (3R,3'R,6'R)-lutein (Table 2) was placed in a thimble (50×10 mm) inside a Micro-Soxhlet extractor (6 ml capacity). The mixture was extracted with 80 ml boiling pentane (b.p.=36° C.) for 4 h. Pentane soluble carotenoids (51 mg) were shown by HPLC to consist of 3'-epilutein (77%), (3R,3'R,6'R)-lutein (19%), total Z-luteins (2.0%), and anhydrolutein (2.0%). Approximately 49 mg of the carotenoids remained as solids in the thimble. This was shown by HPLC to consist of 3'-epilutein (20.0%), (3R,3'R,6'R)-lutein (70.5%), and (3R,3'R)-zeaxanthin (9.5%). Nearly identical results were obtained when extraction was carried out with petroleum ether (b.p.=35–60°).

EXAMPLE 7

Separation of 3'-Epilutein from (3R,3'R,6'R)-Lutein by Enzymatic Acylation with Lipase AK Purification of Starting Material A 1:1 epimeric mixture of (3R,3'R,6'R)-lutein and 3'-epilutein (7 g) prepared from the 70% pure (3R,3'R,6'R)-lutein (Table 2) was purified by flash column chromatography on 150 g of n-silica gel (60–200 mesh size) using 2 liters of a mixture of hexane (70%) and acetone (30%). All the colored fractions were combined to give 5.75 g of a dark orange solid which was shown by HPLC to consist of 3'-epilutein (46.5%), lutein (46.5%), (3R,3'R)-zeaxanthin (5%), total Z-luteins (1%), and anhydrolutein (1%).

0.10 g of this purified mixture of 3'-epilutein and (3R,3'R,6'R)-lutein was suspended in pentane (20 ml), lipase AK (30 mg) from *Pseudomonas fluorescens* ("Amano" 20) and vinyl acetate (50 µl) were added, and the mixture was heated under reflux (36° C.) for 48 h under an atmosphere of nitrogen. After this time, according to HPLC approximately 5% of 3'-epilutein had remained unesterified. The HPLC analysis of the crude product showed the presence of 3'-epilutein-3'-acetate (41.5%), (3R,3'R,6'R)-lutein (46.5%), 3'-epilutein (5%), (3R,3'R)-zeaxanthin (5%), Z-luteins (1%), and anhydrolutein (1%). THF (15 ml) was added and stirring continued for 5 minutes to dissolve all the carotenoids. The enzyme was removed by filtration and the filtrate was evaporated to dryness. The residue was stirred with pentane (30 ml) at 0° C. for 30 minutes and filtered. The solids were washed with cold pentane (10 ml) and dried under high vacuum to give 51.2 mg of a mixture of (3R,3'R,6'R)-lutein (86%), 3'-epilutein (4.7%), and (3R,3'R)-zeaxanthin (9.3%). The pentane soluble fraction was shown by HPLC to consist of mostly 3'-epilutein-3'-acetate as well as minor quantities of (3R,3'R,6'R)-lutein, 3'-epilutein, Z-luteins, and anhydrolutein.

The solvent was evaporated and the pentane soluble fraction was dissolved in THF (10 ml) and treated with 10 ml of methanolic potassium hydroxide (10%). The mixture was stirred at room temperature for an hour and the product was partitioned between water (20 ml) and TBME (20 ml). The water layer was removed and the organic layer was washed with water (2×10 ml), dried over sodium sulfate, and evaporated to dryness. This gave 48.3 mg of a dark red solid which was shown by HPLC to consist of 3'-epilutein (91%), (3R,3'R,6'R)-lutein (4.8%), Z-luteins (2%), and anhydrolutein (2%).

EXAMPLE 8

Separation of 3'-Epilutein from (3R,3'R,6'R)-Lutein by Enzymatic Acylation with Lipase PS A 1:1 epimeric mixture of (3R,3'R,6'R)-lutein and 3'-epilutein (90 mg) prepared from the 97% pure (3R,3'R,6'R)-lutein (Table 2) was suspended in hexane (10 ml). Lipase PS (30 mg) from *Pseudomonas cepacia* ("Amano") and vinyl acetate (50 µl) were added and the mixture was heated under reflux (36° C.) for 72 h under an atmosphere of nitrogen. After this time, according to HPLC only 10% of 3'-epilutein had remained unesterified. The HPLC analysis of the crude product showed the presence of 3'-epilutein-3'-acetate (36.5%), (3R,3'R,6'R)-lutein (46.5%), 3'-epilutein (10%), (3R,3'R)-zeaxanthin (5%), Z-luteins (1%), and anhydrolutein (1%). THF (15 ml) was added and stirring continued for 5 minutes to dissolve all the carotenoids. The enzyme was removed by filtration and the filtrate was evaporated to dryness. The residue was stirred with hexane (30 ml) for 5 minutes and filtered. The solids were washed with hexane (10 ml) and dried under high vacuum to give 41 mg of a mixture of (3R,3'R,6'R)-lutein (80%), 3'-epilutein (9%), and (3R,3'R)-zeaxanthin (11%). The hexane soluble fraction was shown by HPLC to consist of mostly 3'-epilutein-3'-acetate as well as minor quantities of (3R,3'R,6'R)-lutein, 3'-epilutein, Z-luteins, and anhydrolutein. After solvent evaporation, this fraction was re-dissolved in THF (10 ml) and treated with 10 ml of methanolic potassium hydroxide (10%). The mixture was stirred at room temperature for an hour and the product was partitioned between water (20 ml) and TBME (20 ml). The water layer was removed and the organic layer was washed with water (2×10 ml), dried over sodium sulfate, and evaporated to dryness. This gave 45.0 mg of a dark red solid which was shown by HPLC to consist of 3'-epilutein (82%), (3R,3'R,6'R)-lutein (14%), Z-luteins (2%), and anhydrolutein (2%).

EXAMPLE 9

Separation of 3'-Epilutein from (3R,3'R,6'R)-Lutein by Extractions with Supercritical Carbon Dioxide 5 mg of an epimeric mixture of (3R,3'R,6'R)-lutein and 3-epilutein prepared from 97% pure (3R,3'R,6'R)-lutein (Table 2) was mixed with 0.70 g of hydromatrix (mixture of silica gel and diatomaceous earth). This was extracted with carbon dioxide in a Model Prep-Master supercritical fluid extraction apparatus (Suprex-ISCO, Inc., Lincoln, Nebr.). The conditions were as follows: flow=2 ml/min, restrictor temperature=50° C., desorb temperature=10° C., oven temperature=35° C. A two step gradient was employed for extraction of 3'-epilutein. Step one used 100 g of carbon dioxide at 300 atmosphere and step two 50 g of carbon dioxide at 375 atmosphere. Total of 2.4 mg of carotenoids was extracted with this 150 g of carbon dioxide. The extracted carotenoids were shown by HPLC to consist of 3'-epilutein (83%), (3R,3'R,6'R)-lutein (13%), anhydrolutein (2%), and Z-luteins (2%). Approximately 2.5 mg of carotenoids remained in the hydromatrix; these were: (3R,3'R,6'R)-lutein (77%), 3'-epilutein (13%), and (3R,3'R)-zeaxanthin (10%).

EXAMPLE 10

Enrichment of 3'-Epilutein in a Partially Separated Mixture by Low Temperature Crystallization of (3R,3'R,6'R)-Lutein 50 mg of a partially separated mixture of 3-epilutein (86%) and (3R,3'R,6'R)-lutein (14%) containing approximately 2% of other minor carotenoids was dissolved in 7 ml of ethanol in a centrifuge tube. The solution was kept at −70° C. for several hours until (3R,3'R,6'R)-lutein crystallized. The tube was centrifuged and the filtrate was evaporated to dryness to give 21.27 mg of a red solid; this was shown by HPLC to consist of 3'-epilutein (94%) and (3R,3'R,6'R)-lutein (6%). The ethanol insoluble fraction was dried under high vacuum to give 27.5 mg of an orange solid; the composition of the solid was determined by HPLC as: (3R,3'R,6'R)-lutein (20%) and 3'-epilutein (80%).

Summary (3R,3'R,6'R)-Lutein and (3R,3'R)-zeaxanthin are two major dietary carotenoids which have been implicated in the prevention of AMD. While (3R,3'R,6'R)-lutein has been commercially available for a number of years, there are currently no economically viable process for industrial production of dietary (3R,3'R)-zeaxanthin. According to the present invention, (3R,3'R,6'R)-lutein is converted to 3'-epilutein which, in turn, may be converted to (3R,3'R)-zeaxanthin by methods well known in the art. In particular (3R,3'R,6'R)-lutein is epimerized at C-3' in a mixture of a water miscible organic solvent and an aqueous acid at ambient temperature to give almost quantitatively an about 1:1 diastereomeric mixture of 3-epilutein and (3R,3'R,6'R)-lutein. Work-up of the crude product from this reaction can employ an appropriate solvent or solvent mixture to partially separate these diastereomers via preferential crystallization. Depending on the nature of the solvent or solvent mixture, the ratio of 3'-epilutein to (3R,3'R,6'R)-lutein may range from about 3.3 to 4.0. In addition to this preferential crystallization, several other methods have also been developed to effect the separation of 3'-epilutein from (3R,3'R, 6'R)-lutein. These methods include solvent extraction, Soxhlet extraction, enzymatic acylation, and supercritical extraction with carbon dioxide. While some of these methods only result in partial separation of diastereomeric luteins, enzymatic acylation is most effective and yields up to 90% de of 3'-epilutein. A summary of the results for partial separation of 3'-epilutein from (3R,3'R,6'R)-lutein is presented in Table 5.

A poorly separated mixture of diastereomeric luteins may be subjected to low temperature crystallization to obtain 3'-epilutein in 88% de.

TABLE 5

Summary of the results from partial separation of 3'-epilutein from (3R,3'R,6'R)-lutein by different methods.

| Separation Method | 3'-Epilutein (%) | (3R,3'R,6'R)-lutein (%) | de (%) |
|---|---|---|---|
| Solvent Extraction[a] | | | |
| Tert-Butyl methyl ether/Hexane | 78 | 22 | 56 |
| Diethyl ether/Pentane | 77 | 23 | 54 |
| Ethanol | 80 | 20 | 60 |
| Soxhlet Extraction[a] | | | |
| Pentane | 80 | 20 | 60 |
| Petroleum ether, b.p. = 30–60° C. | 80 | 20 | 60 |
| Enzymatic Acylation[b] | | | |
| Lipase AK "Amano" | 95 | 5 | 90 |
| Lipase PS "Amano" 20 | 85 | 15 | 70 |
| Supercritical Extraction With Carbon Dioxide[b] | 86 | 14 | 72 |

[a]employed a 1:1 diastereomeric mixture prepared from 70% pure(3R,3'R,6'R)-lutein,
[b]employed a 1:1 diastereomeric mixture prepared from 97% pure(3R,3'R,6'R)-lutein.

One of the advantages of developing these different methods of separation is the fact that for industrial-scale operations, a simplified combination of these procedures can be employed to improve the yield and purity of 3'-epilutein. For example, the crude products from epimerization of (3R,3'R,6'R)-lutein can be simply enriched in 3'-epilutein during the work-up by solvent manipulation or by preferential crystallization. The resulting diastereomeric luteins, enriched in 3'-epilutein, can then be either subjected to Soxhlet extraction or to enzymatic acylation to further separate this carotenoid from (3R,3'R,6'R)-lutein.

The ready availability of dietary (3R,3'R)-zeaxanthin allows scientists to investigate the role and function of this carotenoid in the prevention of macular degeneration in clinical trials involving patients at a high risk for this disease. In addition to the application of (3R,3'R)-zeaxanthin as a nutritional supplement, this carotenoid can be employed as coloring additives in foods or in animal feeds.

From the foregoing description, one skilled in the art can easily ascertain the essential characteristics of this invention, and without departing from the spirit and scope thereof, can make various changes and modifications of the invention to adapt it to various uses and conditions without undue experimentation. All patents, patent applications and publications cited herein are incorporated by reference in their entirety.

What is claimed is:

1. A method of epimerizing (3R,3'R,6'R)-lutein to give a mixture of (3R,3'R,6'R)-lutein and 3'-epilutein, comprising reacting (3R,3'R,6'R)-lutein in the presence of aqueous acid in a water miscible organic solvent to give a mixture of (3R,3'R,6'R)-lutein and 3'-epilutein.

2. The method of claim 1, wherein the water miscible organic solvent is THF.

3. The method of claim 1, wherein the aqueous acid is aqueous hydrochloric, sulfuric or phosphoric acid.

4. A method of purifying 3'-epilutein from a mixture of (3R,3'R,6'R)-lutein and 3'-epilutein comprising extracting the mixture of (3R,3'R,6'R)-lutein and 3'-epilutein with an organic solvent and recovering the 3'-epilutein from the organic solvent.

5. The method of claim 4, wherein the mixture of (3R,3'R,6'R)-lutein and 3'-epilutein is an about 1:1 mixture of (3R,3'R,6'R)-lutein and 3'-epilutein.

6. The method of claim 4, wherein the organic solvent is a mixture of a non-polar hydrocarbon and a ether.

7. The method of claim 6, wherein the non-polar hydrocarbon is pentane, hexane, heptane or petroleum ether and the ether is diethyl ether, diisopropyl ether or TMBE.

8. The method of claim 4, wherein said extracting is by Soxhlet extraction.

9. A method of purifying 3'-epilutein from a mixture of (3R,3'R,6'R)-lutein and 3'-epilutein comprising low temperature crystallization of the mixture in a $C_{1-4}$ alcohol and recovering the 3'-epilutein from the alcohol.

10. The method of claim 9, wherein the alcohol is methanol, ethanol, propanol or 2-propanol.

11. The method of claim 9, wherein the mixture of (3R,3'R,6'R)-lutein and 3'-epilutein is an about 1:1, mixture of (3R,3'R,6'R)-lutein and 3'-epilutein.

12. A method of purifying 3'-epilutein from a mixture of (3R,3'R,6'R)-lutein and 3'-epilutein comprising:

(a) reacting a mixture of (3R,3'R,6'R)-lutein and 3'-epilutein with an acyl donor in the presence of lipase PS from *Pseudomonas cepacia* or lipase AK from *Pseudomonas fluorescens* in an first organic solvent;

(b) adding a second organic solvent to dissolve the mixture and removing the enzyme by filtration to give a filtrate;

(c) concentrating the filtrate to give a residue;

(d) adding a $C_{5-7}$ hydrocarbon or ether to the residue to give a solution in which 3'-epilutein and 3'-epilutein-3'-acetate are preferentially solubilized;

(e) filtering the solution to give a filtrate;
(f) hydrolyzing the 3'-epilutein-3'-acetate contained in the filtrate to give 3'-epilutein; and
(g) recovering the 3'-epilutein;
thereby obtaining purified 3'-epilutein.

13. The method of claim 12, wherein said hydrolyzing is carried out by treating 3'-epilutein-3'-acetate with alcoholic alkali.

14. The method of claim 12, wherein the 3'-epilutein is recovered by partitioning with water and TBME, separating the TBME from the water and evaporating the TBME.

15. The method of claim 1 wherein the mixture of (3R,3'R,6'R)-lutein and 3'-epilutein is an about 1:1 a mixture of (3R,3'R,6'R)-lutein and 3'-epilutein.

16. The method of claim 12, wherein the first organic solvent is pentane, hexane, TMBE or petroleum ether.

17. The method of claim wherein the second organic solvent is THF, diethyl ether, TBME or diisopropyl ether.

18. The method of claim 12, wherein the hydrocarbon is pentane, hexane or heptane and the ether is THF, diethyl ether, TBME or diisopropyl ether.

19. The method of claim 12, wherein the acyl donor is vinyl acetate or isopropenyl acetate.

20. A method of purifying 3'-epilutein from a mixture of (3R,3'R,6'R)-lutein and 3'-epilutein comprising extracting the mixture with supercritical carbon dioxide and evaporating the carbon dioxide to give purified 3'-epilutein.

21. The method of claim 20, wherein the mixture of (3R,3'R,6'R)-lutein and 3'-epilutein is an about 1:1 mixture of (3R,3'R,6'R)-lutein and 3'-epilutein.

22. A method for producing 3'-epilutein comprising:
(a) epimerizing (3R,3'R,6'R)-lutein to 3'-epilutein in the presence of an aqueous acid in a water miscible organic solvent thereby giving a mixture of (3R,3'R,6'R)-lutein and 3'-epilutein; and
(b) separating 3'-epilutein from (3R,3'R,6'R)-lutein.

23. The method of claim 22, wherein said 3'-epilutein has a de greater than 50%.

24. The method of claim 22, wherein the aqueous acid is aqueous hydrochloric, sulfuric or phosphoric acid.

25. The method of claim 22, wherein the water miscible organic solvent is THF.

26. The method of claim 22, wherein 3'-epilutein is separated from (3R,3'R,6'R)-lutein by low temperature crystallization.

27. The method of claim 22, wherein the (3R,3'R,6'R)-lutein is a crude saponified extract from marigold flowers.

28. The method of claim 22, wherein the (3R,3'R,6'R)-lutein is 70% (3R,3'R,6'R)-lutein.

29. The method of claim 22, wherein the (3R,3'R,6'R)-lutein is 97% pure and is obtained by crystallization of 70% (3R,3'R,6'R)-lutein.

30. The method of claim 27, wherein the crude saponified extract from marigold flowers further comprises several minor carotenoids.

31. The method of claim 22, wherein 3'-epilutein is separated from (3R,3'R,6'R)-lutein by preferential crystallization.

32. The method of claim 22, wherein 3'-epilutein is separated from (3R,3'R,6'R)-lutein by solvent extraction.

33. The method of claim 22, wherein 3'-epilutein is separated from (3R,3'R,6'R)-lutein by Soxhlet extraction.

34. The method of claim 22, wherein 3'-epilutein is separated from (3R,3'R,6'R)-lutein by enzymatic acylation, separation of 3'-epilutein-3'-acetate from (3R,3'R,6'R)-lutein, and alcoholic alkali hydrolysis to give 3'-epilutein.

35. The method of claim 22, wherein 3'-epilutein is separated from (3R,3'R,6'R)-lutein by extraction with supercritical carbon dioxide and evaporation of the carbon dioxide to give the 3'-epilutein.

36. The method of any one of claim 32, 33, 34 or 35, wherein the 3'-epilutein is further purified by low temperature crystallization.

37. The method of claim 31, wherein the preferential crystallization comprises:
(a) treating a mixture of 3'-epilutein and (3R,3'R,6'R)-lutein with a solvent or mixture of solvents giving a 3'-epilutein enriched solution and a (3R,3'R,6'R)-lutein enriched precipitate;
(b) filtering the solution to give a filtrate; and
(c) concentrating the filtrate to give 3'-epilutein.

38. The method of claim 37, wherein the mixture of solvents consists of an ether and a non-polar hydrocarbon.

39. The method of claim 38, wherein the ether is diisopropyl ether, TBME or diethyl ether and the non-polar hydrocarbon is pentane, hexane, heptane or petroleum ether.

40. The method of claim 37, wherein the mixture of 3'-epilutein and (3R,3'R,6'R)-lutein is treated with alcohol.

41. The method of claim 40, wherein the alcohol is ethanol, propanol, 2-propanol or methanol.

42. A method for converting (3R,3'R,6'R)-lutein to a mixture of 3'-epilutein and (3R,3'R,6'R)-lutein comprising:
(a) reacting (3R,3'R,6'R)-lutein with an aqueous acid in a solvent at ambient temperature to obtain a crude product;
(b) neutralizing the crude product; and
(c) removing the water;
thus obtaining a crude diastereomeric crystalline mixture of 3'-epilutein and (3R,3'R,6'R)-lutein.

43. The method of claim 42, wherein the crude product is neutralized by adding aqueous base, and the water is removed by partitioning into an organic solvent, the water is separated and the solvent is evaporated to obtain the crude diastereomeric crystalline mixture of 3'-epilutein and (3R,3'R,6'R)-lutein.

44. The method of claim 43, wherein the base is sodium bicarbonate.

45. The method of claim 43, wherein the organic solvent is TBME, diethyl ether or ethyl acetate.

46. The method of claim 42, further comprising:
(d) extracting the crude diastereomeric crystalline mixture of 3'-epilutein and (3R,3S,6'R)-lutein at ambient temperature thereby precipitating and removing most of the (3R,3'R,6'R)-lutein by filtration, thus obtaining a filtrate comprising 3'-epilutein and (3R,3'R,6'R)-lutein.

47. A method for partial separation of 3'-epilutein from a diastereomeric mixture of 3'-epilutein and (3R,3'R,6'R)-lutein according to the method of claim 42 by extracting the crude crystalline mixture with pentane or petroleum ether (b.p.=35–60° C.) in a Soxhlet apparatus to obtain a pentane or petroleum ether soluble fraction comprising of a diastereomeric mixture of 3'-epilutein (80%) and (3R,3'R,6'R)-lutein (20%), evaporating the solvents to obtain a crystalline mixture enriched in 3'-epilutein.

48. A method for the separation of 3'-epilutein from a mixture of 3'-epilutein and (3R,3'R,6'R)-lutein by enzymatic acylation, comprising reacting 3'-epilutein with vinyl acetate as an acyl donor in the presence of a lipase in pentane, hexane or TBME at 36° C. to convert 95% of 3'-epilutein to 3'-epilutein-3'-acetate while (3R,3'R,6'R)-lutein remains unreacted; subjecting the crude product to hydrolysis with alcoholic potassium or sodium hydroxide at ambient temperature; removing the base by extracting the product with water and an organic solvent; and evaporating the solvent to obtain diastereomeric luteins comprising 95% 3'-epilutein and 5% (3R,3'R,6'R)-lutein as red crystals.

49. The method of claim 48, wherein the (3R,3'R,6'R)-lutein that remains unreacted is separated from 3'-epilutein and 3'-epilutein-3'-acetate by filtration prior to subjecting the crude product to hydrolysis.

50. A method for separating 3'-epilutein from a diastereomeric mixture of 3'-epilutein and (3R,3'R,6'R)-lutein comprising extracting the diastereomeric mixture of luteins with carbon dioxide thereby extracting most of 3'-epilutein with carbon dioxide and leaving behind most of the (3R,3'R,6'R)-lutein thus yielding a product consisting of 86% 3'-epilutein and 14% (3R,3'R,6'R)-lutein.

51. A method for separating 3'-epilutein from a diastereomeric mixture of 3'-epilutein and (3R,3'R,6'R)-lutein comprising low temperature crystallization with an alcohol at −70° C. to crystallize most of the (3R,3'R,6'R)-lutein and increasing the purity of 3'-epilutein in the mother liquor of this crystallization; and evaporation of the alcohol; thus obtaining red crystals containing 94% 3'-epilutein and 6% (3R,3'R,6'R)-lutein.

52. A method of preparing 3'-epilutein-3'-acetate comprising reacting a mixture of (3R,3'R,6'R)-lutein and 3'-epilutein with an acyl donor in the presence of lipase PS from *Pseudomonas cepacia* or lipase AK from *Pseudomonas fluorescens*.

53. The method of claim 52, wherein the acyl donor is vinyl acetate or isopropenyl acetate.

54. A process for obtaining 3'-epilutein, comprising reacting a lutein-containing extract with aqueous sulfuric or phosphoric acid in the presence of tetrahydrofuran, to obtain a 3'-epilutein solution.

55. The process according to claim 54, further comprising reacting said lutein-containing extract with said aqueous sulfuric or phosphoric acid at ambient temperature.

56. The process according to claim 54, further comprising neutralizing the solution.

57. The process according to claim 56, further comprising neutralizing the solution with an aqueous solution of about 5% sodium bicarbonate.

58. The process according to claim 54, further comprising partitioning the 3'-epilutein solution with a second organic solvent.

59. The process according to claim 58, wherein said second organic solvent is methylene dichloride.

60. The process according to claim 54, further comprising washing the 3'-epilutein solution.

61. The process according to claim 54, further comprising washing the 3'-epilutein solution with water.

62. The process according to claim 54, further comprising drying the 3'-epilutein solution with sodium sulfate.

63. The process according to claim 54, further comprising crystallizing the 3'-epilutein by solvent evaporation to obtain 3'-epilutein crystals.

64. The process according to claim 63, further comprising purifying the 3'-epilutein crystals by preparative HPLC.

65. The process according to claim 54, further comprising reacting an extract containing lutein with about 1 N sulfuric acid.

66. A process for obtaining 3'-epilutein, comprising:
    (a) reacting a lutein-containing extract with an aqueous solution of sulfuric acid, in the presence of tetrahydrofuran, to obtain a solution of 3'-epilutein;
    (b) neutralizing the solution;
    (c) partitioning the 3'-epilutein solution with dichloromethane;
    (d) washing the 3'-epilutein solution with water;
    (e) drying the 3'-epilutein solution with anhydrous sodium sulfate;
    (f) crystallizing the 3'-epilutein by evaporation, to obtain 3'-epilutein crystals; and
    (g) purifying the 3'-epilutein crystals by preparative HPLC.

67. The process according to claim 66, wherein the lutein containing extract is reacted with an aqueous solution of sulfuric acid at ambient temperature.

68. The process according to claim 66, further comprising reacting the lutein containing extract with about 1 N sulfuric acid.

69. A process for obtaining optically active (3R,3'R)-zeaxanthin, comprising:
    (a) reacting a lutein-containing extract with an aqueous solution of an inorganic or organic acid in the presence of tetrahydrofuran, to obtain a 3'-epilutein solution;
    (b) neutralizing the solution; and
    (c) reacting 3'-epilutein crystals, with an aqueous alkali metal hydroxide solution.

70. A process for obtaining optically active (3R,3'R)-zeaxanthin, according to claim 69, wherein the inorganic or organic acid is selected from the group consisting of sulfuric acid, phosphoric acid, hydrochloric acid and trifluoroacetic acid.

* * * * *

UNITED STATES PATENT AND TRADEMARK OFFICE
CERTIFICATE OF CORRECTION

PATENT NO. : 6,818,798 B1
DATED : November 16, 2004
INVENTOR(S) : Frederick Khachik It is certified that error appears in the above-identified patent and that said Letters Patent is hereby corrected as shown below:

Columns 1 and 2,
Line 64, delete "(3S,3'S, meso)-Zeaxanthin (Not Dietary)" and replace it with
-- (3S,3'S)-Zeaxanthin (Not Dietary) --.

Column 20,
Line 39, delete "a ether" and replace it with -- an ether --.
Line 52, delete "1:1, mixture" and replace it with -- 1:1 mixture --.
Line 59, delete "an first" and replace it with -- a first --.

Column 21,
Line 12, delete "claim 1" and replace it with -- claim 12, --; and
Line 13, delete "1:1 a mixture" and replace it with -- 1:1 mixture --.
Line 16, delete "claim wherein" and replace it with -- claim 12, wherein --.

Column 22,
Line 3, delete "claim 32, 33, 34 or 35" and replace it with -- claims 31, 32, 33, 34 or 35 --.
Line 44, delete "(3R,3S,6'R)" and replace it with -- (3R,3'S,6'R) --.

Signed and Sealed this

Twenty-eighth Day of February, 2006

JON W. DUDAS
*Director of the United States Patent and Trademark Office*